Figure 1:
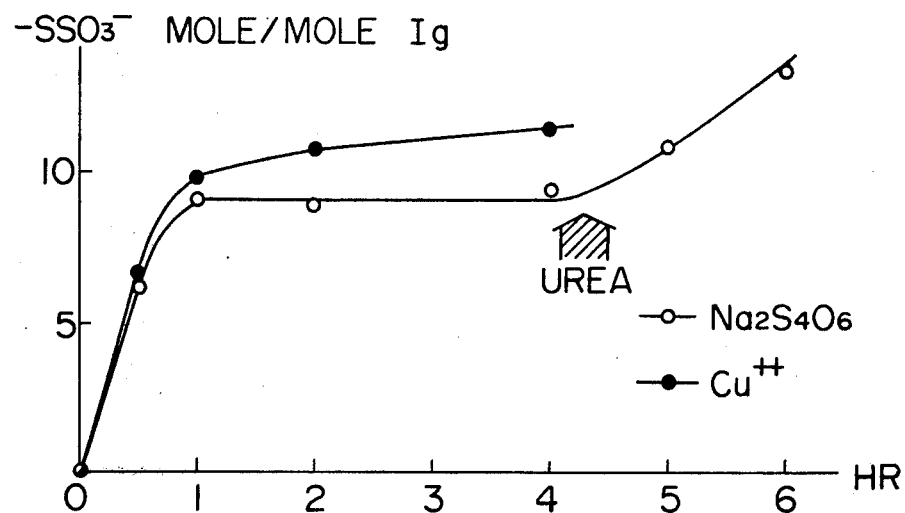

United States Patent [19]

Tomibe et al.

[11] 4,059,571

[45] Nov. 22, 1977

[54] NOVEL IMMUNOGLOBULIN DERIVATIVES AND PROCESS FOR THE PREPARATION THEREOF

[75] Inventors: Katsuhiko Tomibe; Yasuhiko Masuho; Kimihiko Matsuzawa, all of Hino; Sachio Ishimoto, Tokyo; Kazuo Satake, Kawasaki; Tsuneo Watanabe, Tokyo, all of Japan

[73] Assignee: Teijin Limited, Osaka, Japan

[21] Appl. No.: 555,132

[22] Filed: Mar. 4, 1975

[30] Foreign Application Priority Data

Mar. 8, 1974 Japan .................................. 49-26341
June 24, 1974 Japan .................................. 49-71274

[51] Int. Cl.$^2$ ............................................... A23J 1/06
[52] U.S. Cl. ................................................. 260/112 B
[58] Field of Search .................................... 260/112 B

[56] References Cited

U.S. PATENT DOCUMENTS 3,597,409  8/1971  Breuer ............................. 260/112 B

OTHER PUBLICATIONS

F. Franek, Coll. Czech. Chem Commun., 29, 1401, 1964.

*Primary Examiner*—Paul R. Michl
*Attorney, Agent, or Firm*—Sherman & Shalloway

[57] ABSTRACT

Novel immunoglobulin derivatives which are characterized in that in which the interchain disulfide bonds of immunoglobulin are predominantly cleaved, on the average 3 to 5 of the interchain disulfide bonds or the inter- and intra-chain disulfide bonds being cleaved, and so produced sulfur atoms (S-) are S-sulfonated (—S-SO$_3$). The above immunoglobulin derivatives are prepared by reacting native immunoglobulin with A. a compound capable of forming tetrathionate ion, and B. a compound capable of forming in water, sulfite ion whereby cleaving on the average 3 to 5 inter-chain disulfide bonds, or inter- and intra-chain disulfide bonds, of the native immunoglobulin, and S-sulfonating (S-SO$_3$) the so formed sulfur atoms. This invention also provides a water-soluble composition for injection containing said immunoglobulin derivative having the titre of anti-diphtheria of at least 1.0 I.U./ml at its concentration of 10.0% by weight, and a pharmaceutically-acceptable solubilizing agent for said immunoglobulin derivative.

13 Claims, 11 Drawing Figures

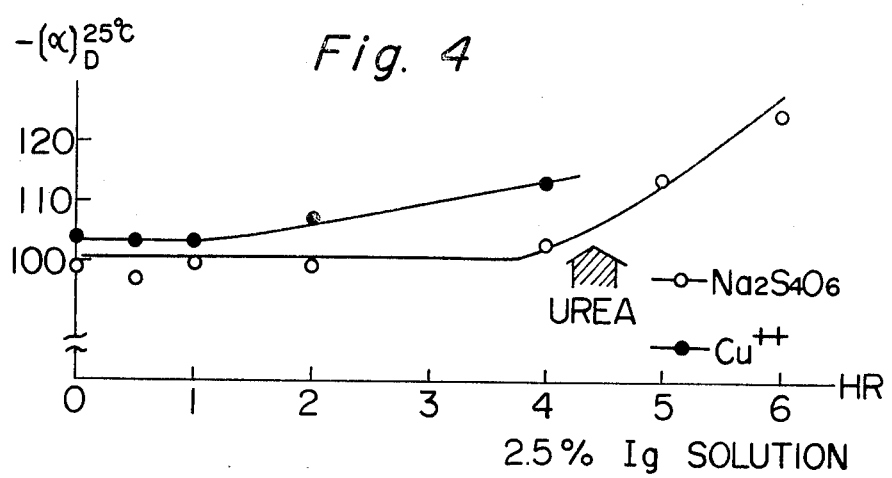
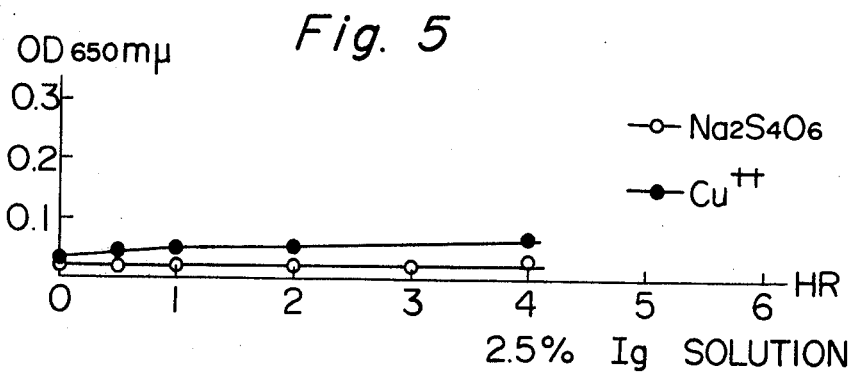
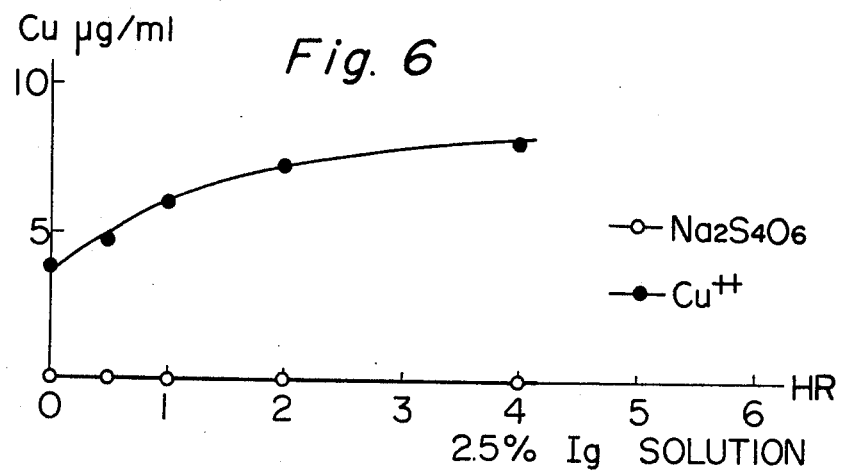

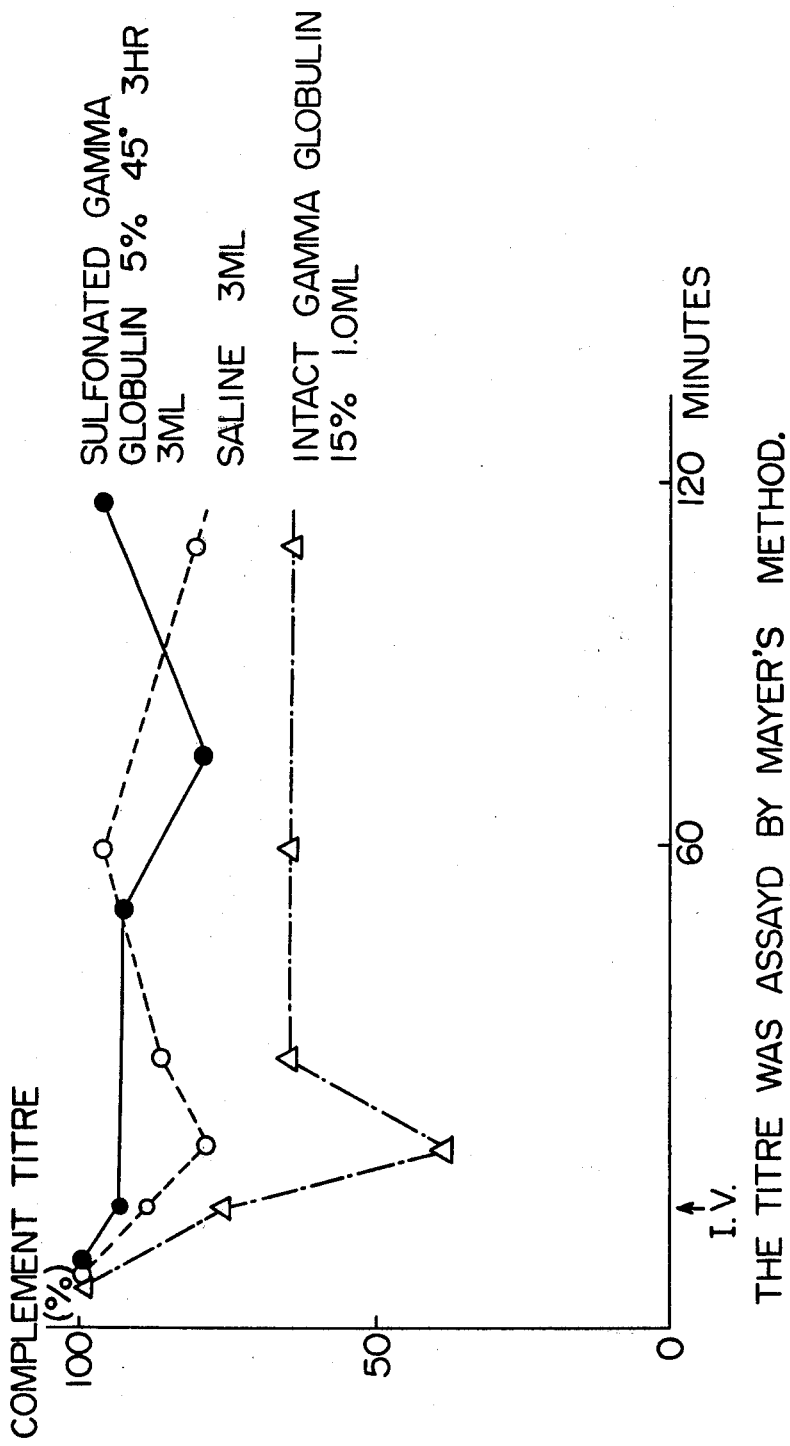
Fig. 10 THE COMPLEMENT TITRE OF GUINEAR PIG AFTER THE INJECTION OF SULFONATED GAMMA GLOBULIN

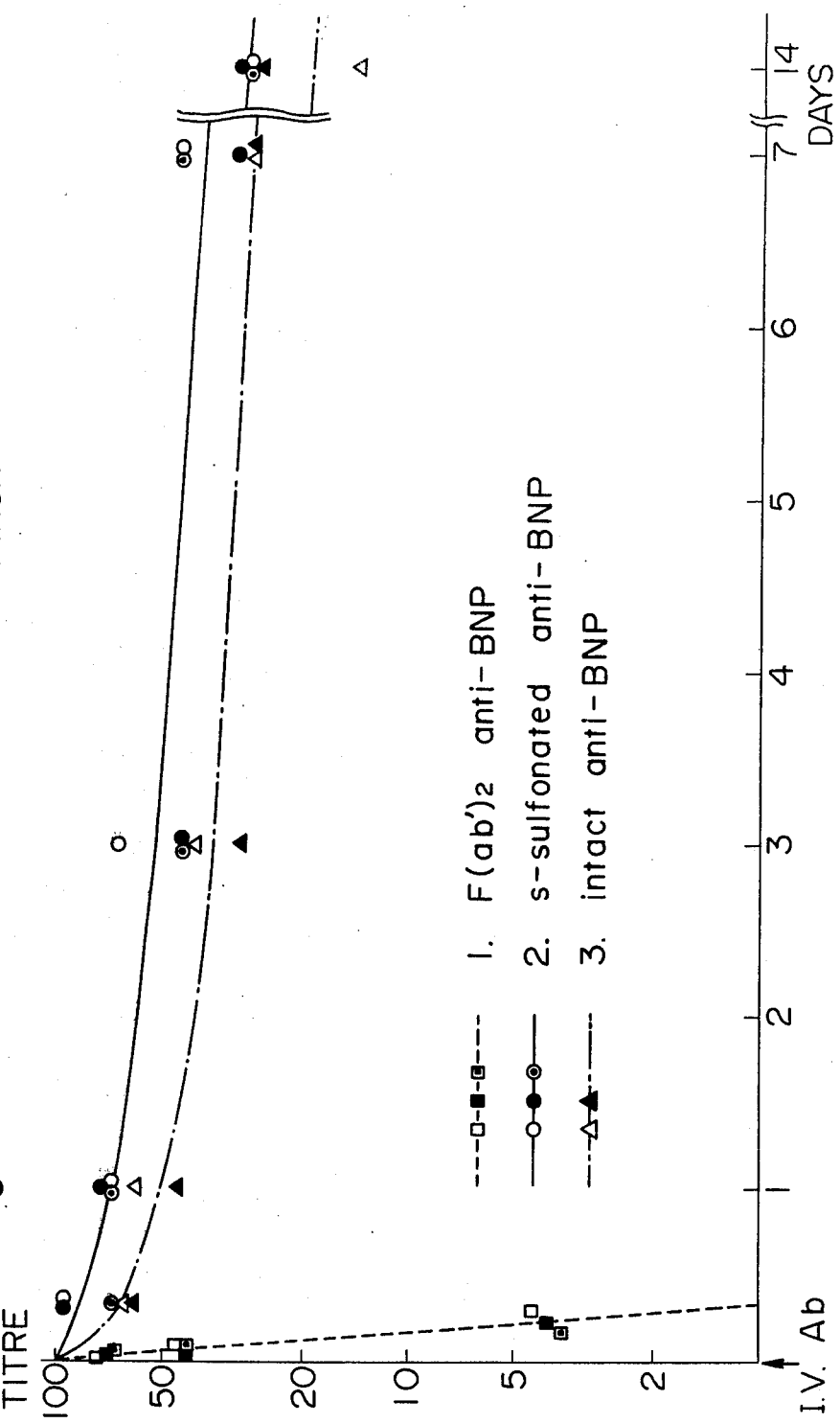

NOVEL IMMUNOGLOBULIN DERIVATIVES AND PROCESS FOR THE PREPARATION THEREOF

This invention relates to novel immunoglobulin derivatives and the aqueous compositions for injection containing said globulin derivatives. The invention also relates to a process for making the novel immunoglobulin derivatives.

With the recent progress in the field of protein chemistry, the correlation of structure with functions of immunoglobulin, which plays an important role for medically extremely significant humoral immunity, is becoming elucidated.

These studies revealed that the immunoglobulin is sub-dividable into five types, i.e., IgG, IgA, IgM, IgD, and IgE, of which IgG occupies no less than 70% by weight.

The immunoglobulins excepting the IgM are each composed mainly of four peptide chains, and several disulfide bonds are present at the interchains and intrachains. For example, said IgG, the most typical of the immunoglobulin, can be fractionated into, when digested with papain, two fragments, "FAB", having antigen-binding activity, and one fragment, "Fc", having complement- and tissue-binding activity. It was furthermore discovered that the IgG is composed of two polypeptide heavy chains (H chains) and two polypeptide light chains (L chains), which are strongly bonded by disulfide bonds and non-covalent bonds to form a protein molecule of approximately 160,000 in molecular weight, and that the molecule contains on the average approximately 4.5 interchain disulfide bonds and approximately 12 intrachain disulfide bonds [B. Frangione & C. Milstein; J. Mol. Biol. 33, 893, (1968)]

Based on the foregoing empirically established facts, various studies have been made concerning immunoglobulin for intravenous injection. The utilization of immunoglobulin has been accomplished by rapid progress upon completion of Cohn's fractionation [E. G. Cohn et al.; J. Amer. Chem. Soc., 68, 459, (1946)]

Cohn et al. fractionated a large amount of human plasma by ethanol precipitation. The fraction II is predominantly IgG, containing a minor amounts of IgA and IgM, and exhibits antibody activity against various microorganisms which cause infectious diseases. Therefore, administration of the fraction II is effective for the prophylaxis and therapy of virus-infection diseases such as measles, viral hepatitis, etc., as well as the infectious diseases from antibiotic-resistant bacteria such as *streptococcus aureaus*.

The sole means heretofore employed for the administration of so fractionated and formulated immunoglobulin has been intramuscular injection. However, the intramuscular injection can effect only partial osmosis of the injection liquid into the body, and is incapable of showing immediate effect. Moreover the intramuscular injection does not allow large quantity-administration. Therefore, production of immunoglobulin suitable for intravenous injection has been desired.

Intravenous injection of known immunoglobulin causes violent pyrogenic and cardiovascular reactions, which are particulally conspicuous with agammaglobulinemic patients. Such untoward reactions of the intravenous injection are caused by the aggregates of immunoglobulin contained in the fractionation of immunoglobulin. The aggregated immunoglobulin binds with complement and tissue, similarly to the antigen-antibody complex, which results in the untoward reactions caused by the anaphylactic factor formed in the body. The untoward reactions can be prevented, therefore, by using the supernatant liquid separated from the formulated immunoglobulin by 100,000 × g ultracentrifugation, but slow re-aggregation, inevitably takes place in the so processed immunoglobulin.

With the view to have safe intravenous injection of immunoglobulin, many studies have been made. In Switzerland an attempt was made to subject the immunoglobulin to pH 4-treatment to temporarily denature its Fc portion and to make the same fit for the intravenous injection [S. Barandun et al.; Vox Sang 7, 157, (1962)]. However the treatment is imperfect, and the untoward reactions are still occasionally observed.

Pepsin-treated immunoglobulin has been commercialized for intravenous injection [H. Koblet, S. Barandun, and H. Diggelman; Vox Sang 13, 92, (1967]. Because 60 – 80% of the treated immunoglobulin is composed of the fragment F($ab'$)$_2$, the injection liquid is quickly degradated in vivo, as demonstrated by its half life of several hours which is one-several tenth of that of the untreated immunoglobulin [B. Jager; Arch. Intern, Med., 119, 60, (1967)]. Still improved injection liquid can be provided by replacing the papsin by plasmin as the treating agent, but the method has the drawback in that the plasmin cannot be later eliminated [L. A. Hanson & B. G. Johonson; Int. Arch. Allergy 31, 380, (1967)].

Recently it has been proposed to selectively cleave mainly the interchain disulfide bonds of immunoglobulin and S. alkylate the produced sulfur atoms (S—), and to use the immunoglobulin derivatives showing reduced untoward reaction for the intravenous injection.

For instance, as one of the attempts to cleave the interchain disulfide bonds of immunoglobulin to obtain polypeptide chains, the method of S. T. Stevenson et al. (Bio. Chem., J. 118, 703, 1960) is known, which comprises reducingly cleaving interchain disulfide bonds of human immunoglobulin G in dithiothreitol, and S-alkylating the same in iodoacetoamide. The method, however, requires two-stage reactions, and furthermore the product is S-alkylated polypeptides which have the potential danger of new antigenecity. Again, it is by no means easy to convert the S-portion to thiol group. Therefore, it is also difficult to derive therefrom a useful reagent by supporting the same on a carrier such as a suitable polymer, utilizing active thiol.

Franek's method [F. Franek, Coll. Czech. Chem. Commun., 29, 1401, (1964)] comprises treating porcine immunoglobulin with sodium sulfite and cupric ion to form S-sulfonated polypeptides.

However, our reproducing experiments of the above method of Franek et al. revealed such deficiencies inherent in the method, as i. that the resulting denatured polypeptides contain copper of cupric ion, the elimination of the copper or cupric ion from the product being extremely difficult or substantially impossible, ii. that the denatured polypeptides exhibit rapidly reduced antigen-binding activity, if they could have the desired low anticomplement activity, and iii. that the original conformity of immuniglobulin is distorted and changed, as confirmed by the optical rotation measurement, as demonstrated by the Controls given later in this specification.

The fact that it is substantially impossible to eliminate the minor residual copper from the denatured polypeptide product of the Franek et al.'s method signifies that said product is thermally unstable, is apt to form aggregates, and apparently is physiologically undesirable when used for the intravenous injection [D. A. Derber; Arthritis and Rheumatism, 17, 85, (1974)].

Accordingly, an object of the present invention is to provide novel immunoglobulin derivatives containing no copper or cupric ion, in which either the interchain disulfide bands linking the two polypeptide heavy chains (H chains) and two polypeptide light chains (L chains) in the immunoglobulin are selectively cleaved or, besides the specified interchain disulfide bonds, a part of the intrachain disulfide bonds are cleaved, and the cleaved sulfur atoms (-S) are S-sulfonated; as well as to provide aqueous compositions for injection containing the novel immunoglobulin derivatives, and the processes for their preparation.

Still another object of the invention is to provide novel immunoglobulin derivatives which have reduced anticomplement activity and can maintain excellently high antibody activity for prolonged periods in the human body; and the process for the preparation thereof.

A further object of the present invention is to provide novel immunoglobulin derivatives which exhibit little adverse reactions and excellent antibody activity, and can re-construct the native immunoglobulin in vivo; the intravenously injectable compositions containing the novel derivatives, and the processes for their preparation.

A further object of the present invention is to provide novel immunoglobulin derivatives formed by selectively cleaving substantially only the interchain disulfide bonds linking the heavy chains (H chains) and light chains (L chains) of the immunoglobulin, and substantially S-sulfonating the formed sulfur atoms; the aqueous compositions for intravenous injection containing the same; and the processes for their preparation.

Still another object of the invention is to provide a process for making the above-specified immunoglobulin derivatives of uniform quality with stability.

According to the present invention, the foregoing objects and advantages are accomplished by the novel immunoglobulin derivatives in which the interchain disulfide bonds of native immunoglobulin are predominantly cleaved to effect the cleavage of, on the average, 3 to 5 interchain disulfide bonds, or the interchain and intrachain disulfide bonds, and thereby produced sulfur atoms (-S) are S-sulfonated (-S-SO$_3$).

Particularly the novel immunoglobulin derivatives of the invention are characterized in that on the average approximately 3 to 4.5, inter alia, approximately 4.5, of substantially the interchain disulfide bonds of native immunoglobulin are selectively cleaved, and that the so cleaved sulfur atoms are S-sulfonated, and also in that it contains substantially no oxidizing metal ions such as cupric ion.

Again, if specified without regard to the sites of cleaved disulfide bonds, the novel immunoglobulin derivatives of the invention are characterized in that:

1. they are formed by cleaving, on the average, 3 to 5 interchain, or 3 to 5 interchain and intrachain, disulfide bonds of native immunoglobulin, and S-sulfonating (-S-SO$_3$) the thus cleaved sulfur atoms, and that 2. the immunoglobulin derivative contains at least 1.0 I.U./ml of the titre of ati-diphtheria at its concentration of 10.0% by weight.

The immunoglobulin derivatives of the invention can provide water-soluble compositions useful for making injection liquids, when blended with their solubilizing agents which are harmless to man. Also by dissolving the water-soluble compositions in water, aqueous compositions for intravenous injection can be provided.

Particularly preferred immunoglobulin derivative according to the invention is that in which on the average substantially 4.5 interchain disulfide bonds of native immunoglobulin are cleaved, and the so produced sulfur atoms (substantially 9 atoms on the average) are S-sulfonated (-S-SO$_3$). According to our studies, such preferred immunoglobulin derivative is formed when the interchain disulfide bonds alone linking the H chains and L chains of native immunoglobulin are substantially cleaved, and the so produced sulfur atoms are S-sulfonated.

The novel immunoglobulin derivatives of the invention can be prepared by reacting native immunoglobulin with A. a compound capable of forming tetrathionate ion, and B. a compound capable of forming sulfite ion, in water, to cleave on the average 3 to 5 of the interchain disulfide bonds, or the inter- and intra-chain disulfide linkages, of native immunoglobulin, and concurrently S-sulfonating (-S-SO$_3$) the so produced sulfur atoms.

According to the subject process as above-described, it is possible to first cleave the interchain disulfide bonds of native immunoglobulin predominantly.

Therefore, the immunoglobulin derivatives according to the invention, in which average 3 to 4.5 intramolecular disulfide bonds of native immunoglobulin are cleaved and the produced sulfur atoms are S-sulfonated, can be regarded as the product wherein substantially the interchain disulfide bonds alone of the native immunoglobulin are cleaved and the resulting sulfur atoms are S-sulfonated.

The process according to the invention is essentially performed in water, but the medium is by no means limited to water, but any other aqueous medium may be used so long as it is in no way detrimental to the reaction of this invention.

According to the invention, native immunoglobulin is reacted with

A. a compound capable of forming tetrathionate ion, and

B. a compound capable of forming sulfite ion, in water, to have its average 3 –4.5 interchain disulfide bonds cleaved or, in addition to substantially all of the interchain disulfide bonds, a minor amount of interchain disulfide bonds cleaved, the number of cleaved intramolecular disulfide bonds not exceeding, at the maximum and on the average, 5; and to have substantially all of the so produced sulfur atoms S-sulfonated.

As the compound (A) which is capable of forming tetrathionate ion in water, tetrathionic acid, alkali metal salt thereof such as sodium tetrathionate, potassium tetrathionate, etc., and water-soluble salts thereof such as ammonium tetrathionate, are preferred, while any other compound may be used so far as it can form tetrathionate ion in water.

Also typical examples of the compounds (B) which can provide sulfite ion in water include sulfurous acid, sodium sulfite, potassium sulfite, and sodium bisulfite, but any other compound may be used so far as it can form sulfite ion in water.

The compound (A) which is capable of forming tetrathionate ion in water acts as an oxidizing agent. Whereas, the compound (B) which forms sulfite ion in water serves as a reducing agent as well as S-sulfonating agent.

The amounts of the sulfite ion and tetrathionate ion should be each no less than 2 molar times the interchain, or inter- and intra-chain disulfide bonds (-S-S-bond) of the starting native immunoglobulin to be cleaved. It may be as much as each 100 molar times the bonds to be cleaved, or even more.

It is preferred that the compounds (A) and (B), particularly (B), are dissolved in water or a buffer solution, in advance of their addition to the reaction system of this invention.

The reaction taking place according to the subject process may be described as that, the interchain disulfide bonds of native immunoglobulin are cleaved by the sulfite ion, one of the sulfur atoms being converted to S-sulfonate group ($-S-SO_3$), and the other, to thiol group (-SH), and each two of the so formed thiol groups are oxidized by tetrathionate ion to form disulfide bond; or, the thiol group reacts with tetrathionate ion to be converted to S-thiosulfate ($-S-S_2O_3$), and again attacked by the sulfite ion. Thus the reaction is repetitive. As the result of such reaction, the interchain disulfide bonds of native immunoglobulin are cleaved and thereby separated sulfur atoms are each converted to S-sulfonate group ($-S-SO_3$) in the heavy chains and light chains.

The process of this invention is preferably performed at temperatures not higher than 50° C., particularly 10° - 50° C., inter alia, 15° - 48° C., while it is permissible to practice the process at lower temperatures.

Normally at high temperatures exceeding 50° C., particularly above 55° C., the native immunoglubulin is apt to be denatured, and cleavage of intrachain disulfide bonds starts to take place. Therefore such high temperatures should be avoided.

In the subject process, presence of such protein-perturbing agent as urea or guanidine which are employed in S-sulfitolysis of insulin or ribonuclease [J. L. Bailey et al. J. Biol. Chem., 234, 1733 (1959)] should rather be avoided. If used, however, the quantitative ratio of such perturbing agent should be no more than 2.0 mols per mol of the native immunoglobulin.

The reaction time differs depending on such factors as the type of immunoglobulin, amount of reagent, reaction temperature, and the presence of a denaturating agent such as urea or the like. The preferred pH value of the reaction liquid ranges from approximately 3.5 to 10, particularly 6 to 9. At the pH lower than 3.5, cleavage of intrachain disulfide bond in the Fc portion of native immunoglobulin tends to take place. Whereas, at the pH exceeding 10, the globulin-constituting protein is denaturated, which invites such objectionable results as inhibition of anticomplement activity reduction and reduction of antigen-binding activity.

There is no critical order for the addition of reagents to the reaction system of the present invention.

After the reaction the reaction mixture is subjected to consecutive dialysis against water and a suitable buffer solution such as saline containing 0.01 M phosphate buffer (pH 7.4) and 2.5% glycine, to thereby provide the novel immunoglobulin derivatives of the present invention.

The novel immunoglobulin derivatives of the invention furthermore can be separated into the L chains and H chains, by column chromatography using the column filled with suitable resins, for example, Sephadex G-75 column and a solvent such as 1M propionic acid, for example.

While the preferred conditions for practicing the subject process having been described so far, the process is by no means restricted by the afore-specified conditions.

In short, it is within the coverage of the subject process, so long as the native immunoglobulin is contacted with A. tetrathionate ion, and B. sulfite ion in water as aforesaid, and the reaction is advanced to cause cleavage of predominantly the interchain disulfide bonds of native immunoglobulin and S-sulfonation of the sulfur atoms freed upon the cleavage.

The number of S-sulfonate ($-S-SO_3$) groups in the novel immunoglobulin derivative of the invention can be determined, for example, by practicing the subject process using radio-active sodium sulfite, and measuring the S-sulfonates labelled with $^{35}S$ in the resulting immunoglobulin derivative with a liquid scintillation counter, as demonstrated in the later given Examples. One-half of the average number of the labelled S-sulfonate groups per molecule of the immunoglobulin derivative so determined corresponds to the average number of cleaved intramolecular disulfide bonds in the starting native immunoglobulin.

On the other hand, the immunoglobulin derivatives containing average approximately 9 S-sulfonate groups per molecule, i.e., that formed by cleaving average 4.5 disulfide linkages of native immunoglobulin and S-sulfonating the produced sulfur atoms according to the invention, can be fractionated into the H chains and L chains, using, for example, Sephadex G-75 or G-200 column, preferably in the presence of a minor amount of urea or guanidine, with propionic acid solvent, as aforesaid.

Therefore, any set of conditions can be employed for the subject process, so long as they allow the production of the immunoglobulin derivatives containing average substantially 9 S-sulfonate groups per molecule, which further can be fractionated into H chains and L chains by the specified column chromatography. Once such set of conditions are empirically determined, the number of cleaved disulfide linkages in the native immunoglobulin can be suitably controlled by adjusting the reaction time under the selected set of conditions.

Hereinafter the present invention will be more specifically explained with reference to the working Examples, with the proviso that they should never be construed to limit the invention herein disclosed in any way, since they are given for the sole purpose to assist better understanding of the invention.

The reagents employed in the Examples were as follows:

o Human immunoglobulin I: 15% solution of human immunoglobulin for intramuscular injection in buffered saline (pH neutral) containing 2.5% glycine, product of the Chems-Sero-Therapeutic Research Institute.

o -Globulin-Human Fr, II(human immunoglobulin II) produced by Nutritional Biochemicals Corporation (U.S.A.).

o Sodium tetrathionate: that prepared immediately before the use from sodium thiosulfate ($Na_2S_2O_3 \cdot 5H_2O$) and iodine ($I_2$) in aqueous ethanol.

o Sodium sulfite: special rade chemical produced by Komune Kagaku Yakuhin, Co.

o $Na_2SO_3$ labelled with $^{35}S*$: product of New England Nuclear (U.S.A.)

o Tris HCl: Tris(hydroxymethyl) aminomethane produced by Nakarai Kagaku Yakuhin Co., a special grade chemical for biochemical research with pH reduced with aqueous 1N-HCl.

Antibody activity and anticomplement activity levels were measured as follows:

Measurement of the titre of anti-diphtheria
  Reaction: Sensitized possive hemagglutination reaction (note 1) was utilized
  Method of Measurement: Microplate process
  Blood cells: Human O-type red blood cells (note 2) which had been treated with formalin were BDB (Bis-diazo-benzidine)-treated (note 3) and sensitized with diphtheritic toxoid.
  Control: Standard antibody to diphtheria (NIH Japan).
  note (1) NIH Japan method: R. Murata, No. 21 Tokyo Veterinaian & Animal Husbandry ('75)
  note (2) W. T. Butler: J. Immunol. 90 663 ('63).
  note (3) J. Dordon, B. Rose, A. H. Sehon: J. Exp. Med. 108, 37, ('58).

Measurement of antibody to measles, rubella, and mumps (notes 4 – 9)
  Reaction: Microplate process excepting measles for which test tube method was employed.
  Antigen: Antigens for hemagglutination produced by Toshiba Chemicals
  Control serum: standard antiserum produced by Toshiba Chemicals, excepting the measles for which standard antiserum (NIH Japan) was used.
  note (4) Duide por Hemagglutination Inhibition Test for Measles by Microtitre Method: NIH Japan
  note (5) Sequence for Measuring Human Immunoglobulin is Antibody Activity to Measles: NIH Japan
  note (6) T. Toyama, Clinical Examinations, 16 No. 2 9 ('72).
  note (7) An Introduction to Virus Empirical Science: ed. by NIH Japan Alumni. pub. by Maruzen Bookstore ('73).
  note (8) Recommended Specifications for Microbiological Reagents U.S. Dept. of HEW, April, 1965.
  note (9) Mumps HI Reaction Techniques, NIH Japan.

Measurement of anticomplement activity: The method described in Kabat & Mayer, "Experimental Immunochemistry "p. 225 ('61) was used. One percent immunoglobulin solution containing guinea pig serum, 20 $CH_{50}$/ml, was made into 5 ml with GVB++ heated at 37° C. for an hour, and the consumed anticomplement was measured by said method. The anticomplement activity levels are indicated by the percentages of consumption to 20 $CH_{50}$/ml.

EXAMPLE I (Correlations of reaction conditions with number of cleaved disulfide bonds)

Condition I

To 51 mg of afore-specified human immunoglobulin II, 36 mg of $^{35}S$-labelled $Na_2SO_3*$, and 22 mg of $Na_2S_4O_6$, an aqueous 0.1M tris-HCl (pH 8.2) was added to provide a sample of 5.0 ml, which was heated to 45° C., and the subsequent reaction was conducted at said temperature. Each 0.5 ml of the reaction mixture was sampled immediately after initiation, and after 30 minutes, 1 hour, 2 hours, 4 hours, 7.4 hours, and 24 hours of the reaction. Each of the samples was mixed with 10 ml of 50% saturated ammonium sulfate under ice-cooling, allowed to stand for 15 minutes under ice-cooling, and the resulting precipitate was centrifugally separated. After washing with again 50% saturated ammonium sulfate, the precipitate was measured of its radioactivity with liquid scintillation counter, and from the result the number of —S-$SO_3$ groups contained therein was calculated.

Condition II

The reaction was started under identical conditions with those of above Condition I, without sampling during the reaction. 4 hours after the reaction began, an aqueous 10 M urea solution was added to the reaction system to make the urea concentration in the latter 4M. After 5 and 6 hours reaction (1 and 2 hours reaction after the urea addition, respectively), each 0.5 ml of the reaction liquid was sampled, and treated similarly to the samples taken under Condition I.

Condition III

The reaction and sample treatment of Condition I were repeated except that the reaction temperature was 0° C.

Condition IV

The reaction and sample treatment of Condition I were repeated except that the reaction temperature was 25° C.

Condition V

The reaction and sample treatment of Condition I were repeated except that no $Na_2S_4O_6.2H_2O$ was used.

The results of reactions under the foregoing Conditions I, II, III, IV, and V are collectively shown in Table 1 below.

Table 1

(Correlation of Reaction Conditions with Number of —S—$SO_3$ Groups Formed)

| Reaction Condition | Reaction Time (hr) 0 | 0.5 | 1 | 2 | 4 | 5 | 6 | 7.4 | 24 |
|---|---|---|---|---|---|---|---|---|---|
| I (45° C) | 0 | 6.1 | 9.0 | 8.9 | 9.4 | — | — | 8.9 | 10.4 |
| II (45° C, urea added after 4 hours) | — | — | — | — | — | 10.9 | 13.3 | — | — |
| III (0° C) | 0 | 0.5 | 1.6 | 2.5 | 2.9 | — | — | 3.4 | 5.0 |
| IV (25° C) | 0.2 | 1.6 | 4.1 | 5.0 | 4.5 | — | — | 7.0 | 8.5 |
| V ($Na_2S_4O_6$.$2H_2O$ free) | 0 | 0.5 | 0.8 | 1.1 | 0.8 | — | — | — | 4.5 |

Incidentally, the number of cleaved disulfide bonds corresponds to one-half of the number of -S-$SO_3$ groups.

From the results of reaction shown in Table 1 above, the following is concluded. When the subject process is practiced in the presence of tetrathionate and sodium sulfite, at 45° C. Under Condition 1, approximately 3 disulfide bonds were cleaved, which reached an average of approximately 4.5 during 1 to 7 hours reaction, and approximately 5.2 after 24 hours reaction.

When the reaction was carried out in the identical manner except at 25° C. (Condition IV), the number of disulfide bonds cleaved was reduced, the number of cleaved bonds reaching on the average approximately 4.3 after as many as 24 hours reaction. When the reaction temperature was 0° C. (Condition III), the average number of cleaved disulfide bonds still decreased. However in the absence of sodium tetrathionate (Condition V), the cleavage of disulfide bonds failed to progress smoothly. Whereas, when urea was added to the reaction system (Condition II), the average number of cleaved disulfide bonds rapidly increased after the urea addition:

EXAMPLE 2

(Comparison of physical property deterioration when $Na_2S_4O_6$ or $Cu^{++}$ was used as the oxidizing agent)

Condition I

To 2.0 g of previously specified human immunoglobulin II, 1.42 g of $Na_2SO_3$, and 0.86 g of $Na_2S_4O_6.2H_2O$, 0.1M tris HCl (pH 8.2) was added to make a 200 ml mixture, which was reacted at the initiating temperature of 45° C. Immediately after the reaction started, and at 30 minutes, 1 hour, 2 hours, and 4 hours thereafter, each 15 ml of the reaction liquid was sampled. Immediately following the fifth sampling, 10M urea solution was added to the remainder of the reaction liquid to make the urea concentration therein 4; M, and the reaction was continued. After 5 and 6 hours reaction (1 and 2 hours reaction after the urea addition) each 22.5ml of the reaction liquid was sampled, and to which 22.5 ml of ice-cooled saturated ammonium sulfate was added, followed by 30 minutes standing under cooling with ice. The resulting precipitate was centrifugally separated and washed with a 50% saturated ammonium sulfate, and dialyzed for 24 hours against buffered saline of pH 7.4, through a Visking tube. After the dialysis samples of each required amount for specific analysis were taken, which were diluted with buffered saline of pH 7.4 containing 2.5% glycine, and analyzed.

Condition II

The reaction and treatments under Condition I were repeated except that $Na_2S_4O_6.2H_2O$ was replaced by 50 mg of $CuSO_4.5H_2O$, and the reaction was terminated at the end of the 4th hour.

Figure 2:
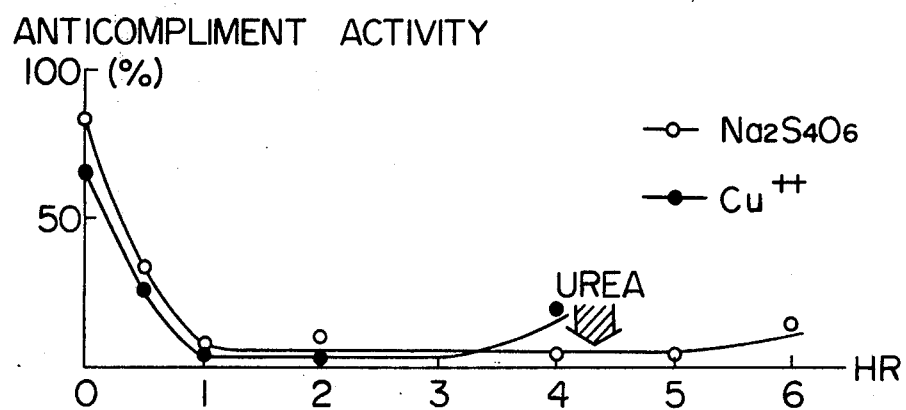
Figure 3:
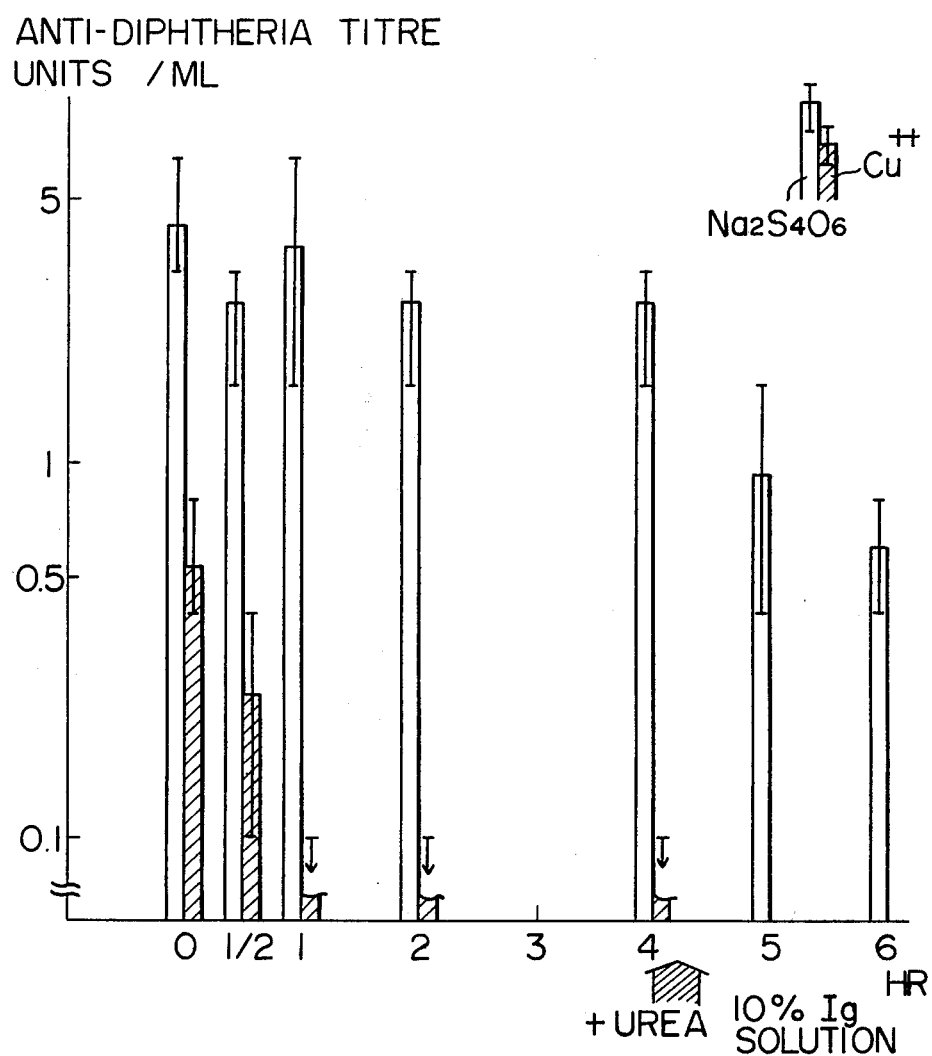

Thus obtained solutions of the various immunoglobulin derivatives were subjected to the following tests and measurements.

a. Correlation of reaction time and the number of —S-$SO_3$ groups:

The numbers of —S-$SO_3$ groups in the samples oxidized with tetrathionate ($Na_2S_4O_6.2H_2O$) are plotted in FIG. 1 by blank circles (o), concurrently with the similar data obtained under Conditions I and II of Example 1. The data of other samples oxidized by $Cu^{++}$ which were reacted and treated in identical manner with the Condition I of Example 1 excepting that $Na_2S_4O_6.2H_2O$ was replaced by 50 mg of $CuSO_4. 5H_2O$, are plotted in FIG. 1 with black dots (o).

b. Correlation of reaction time with anticomplement activity:

The anticomplement activities of the samples obtained by the oxidation with $Na_2S_4O_6.2H_2O$ under Condition I of Example 2 measured by the already specified method are plotted in FIG. 2. Also the anticomplement activities of the samples oxidized with $Cu^{++}$ under Condition II are shown in FIG. 2. It can be understood from FIG. 2 that the anticomplement activities of all the samples were reduced to no higher than 30% after reaction for 30 minutes.

c. Correlation of reaction time with the titre of antidiphtheria:

The same employed in (b) above was measured 3 times of its titre of antidiphtheria by the method already specified. The deviation and mean values are shown in FIG. 3. From the graph it can be understood that the samples oxidized with $Cu^{++}$ show the titre already no higher than 0.3 IU after reaction for 30 minutes.

d. Correlation of reaction time and optical rotation:

The same samples employed for the anticomplement activity measurement of (b) above (protein concentration 2.5%) were measured of their optical rotation, with the results as shown in FIG. 4. From the shown results it can be understood that the presence of cupric ion in the reaction system causes progressive denaturation during the reaction, and that the presence of urea promotes the denaturation, as demonstrated by the conspicuous increase in the optical rotation.

Figure 7:
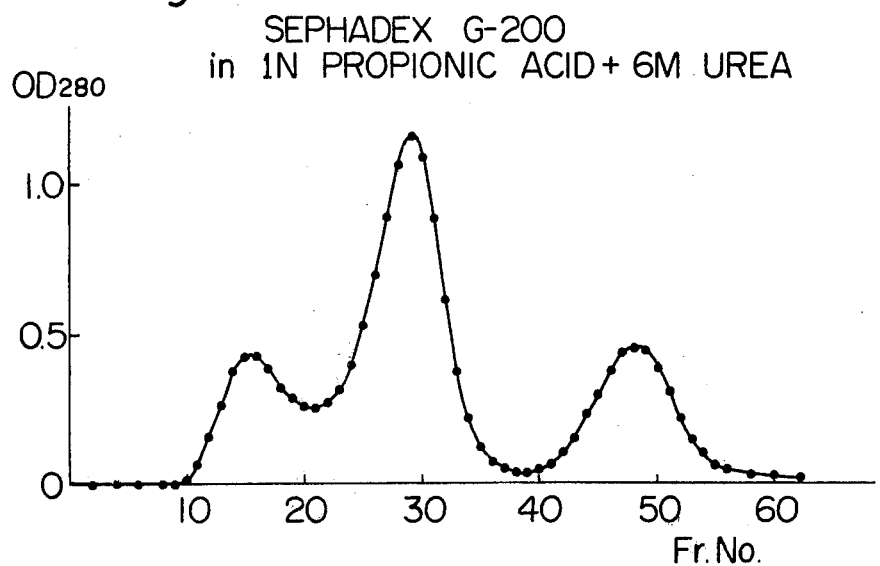

Incidentally, the optical rotation was measured at 25° C., using a 1-cm cell.

e. Correlation of reaction time with turbidity after heat-treatment:

The same samples employed for the anticomplement activity measurement in (b) were heat-treated in air for 4 hours at 50° C., at the concentration of 2.5%, with the results as shown in FIG. 5. As is apparent from FIG. 5, the presence of only a very minor amount of cupric ion causes deterioration of heat stability and promotes the tendency for aggregation.

f. Correlation of reaction time with copper content:

The same samples employed for the anticomplement activity measurement in (b) were determined of their cupric ion content by atomic absorption analysis, with the results as shown in FIG. 6. From the results it can be understood that when cupric ion is employed, even washing and dialysis of the sample cannot eliminate the cupric ion.

g. Separation of heavy chains from light chains:

The same sample with that taken after 2 hours reaction under Condition I of Example 2 was dialyzed for 24 hours with 1N-propionic acid containing 6M urea, and subjected to Sephadex G 200 column (1.5 $\phi$cm × 80 cm) chromatography equilibrated with the specified aqueous solution, with the results as shown in FIG. 7. The first peak from the left of same graph denotes $H_2L_2$ chains not yet separated, the second peak, H chains, and the third peak, L chains. The graph proves that the sample was separated into H chains and L chains.

Summarizing the results demonstrated in FIG.'s 1 through 7, the following conclusions can be reached.

1. As demonstrated by the results of Condition I experiments in Example 1, when the subject process is practiced in the presence of tetrathionate and sulfite ions, at any length of reaction time ranging from 1 to 4 hours, the average number of cleaved disulfide linkages is approximately 4.5, and so produced sulfur atoms are S-sulfonated (average number of S-sulfonate groups, approximately 9) to form the S-sulfonated immunoglobulin (FIG. 1) which is separable into H chains and L chains by means of, for example, chromatography with Sephadex G 200 column (FIG. 7) and has substantially identical optical rotation with that of native immunoglobulin (FIG. 4).

From the foregoing results, the novel immunoglolin derivative can be safely assumed to be that formed by substantially the cleavage of interchain disulfide bonds only of native immunoglobulin and S-sulfonation of the cleaved sulfur atoms, in consideration of the fact that the number of interchain disulfide bonds of native immunoglobulin is on the average 4.5.

And, such immunoglobulin derivative has the anticomplement activity reduced to no higher than 10%, far lower than that of the native immunoglobulin (FIG. 2), but exhibits the titre of anti-diphtheria not appreciably inferior to that of native immunoglobulin, as demonstrated by the nearly equivalent antigen-binding activity. As shown in FIG. 3, at the concentration of 10 wt%, the immunoglobulin derivative maintains the antigen-binding activity of at least 1.0 IU/ml.

2. Those S-sulfonated immunoglobulin derivatives formed by cleavage of less or more than 4.5, on the average, of disulfide bonds of native immunoglobulin, for example, on the average no less than 3 or as many as 5, and S-sulfonation of the sulfur atoms, show somewhat less reduction in their anticomplement activities and inferior antigen-binding activity compared with those of the preferred immunoglobulin derivative described in above item 1) (FIGS. 2 and 3), but still exhibit appreciably improved anticomplement activity over that of native immunoglobulin.

3. Whereas, when tetrathionate ion as the oxidizing agent is replaced by cupric ion, the resulting immunoglobulin derivatives contain the cupric ion although at very low concentrations which tend to increase as the reaction time becomes longer (FIG. 6). Also the number of cleaved disulfide bonds of native immunoglobulin increases with the prolongation of reaction time (FIG. 1), and consequently it is difficult to produce the object immunoglobulin derivative by cleaving average substantially 4.5 disulfide bonds of native immunoglobulin with stability.

Furthermore, the immunoglobulin derivatives obtained with the use of cupric ion do show reduced anticomplement activity (FIG. 2), but simultaneously their anti-diphtheria titre is conspicuously decreased compared with that of native immunoglobulin. Thus their antigenbinding activity is extremely reduced (FIG. 3). The immunoglobulin derivatives again show, when the reaction time exceeds 1 hour, different optical rotations from that of native immunoglobulin, which signifies that structural changes occurred in their constituent protein.

4. Similar changes in optical rotation are also observable with the immunoglobulin derivatives produced in accordance with the subject process but urea is added in the way of reaction. For this reason also the absence of urea, guanidine, and the like in the reaction system is recommended.

EXAMPLE 3

(Selective cleavage of interchain disulfide bonds)

Two (2) ml of an aqueous solution containing 20mg of human immunoglobulin I, 80 mg of 35S-$Na_2SO_3$* (8.22 × $10^{11}$ dpm/mol), and 40 mg of $Na_2S_4O_6.2H_2O$, was adjusted of the pH to 7.2 with AcOH, and reacted at 39° C. for 2 hours. Thereafter the reaction liquid was dialyzed against 5 liters of water for 24 hours. Then urea and propionic acid were slowly added to the system to the final concentrations of 4M and 1N, respectively. As the sample before the charging into chromatocolumn, 0.1 ml of the solution was taken, the data thereof being shown at the left side of the axis of ordinates in FIG. 8. The remainder of the system was subjected to the chromatography using the Sephadex G200 column (1.5 $\phi$ cm × 100 cm) equilibrated with 1N propionic acid containing 4M urea.

Figure 8:
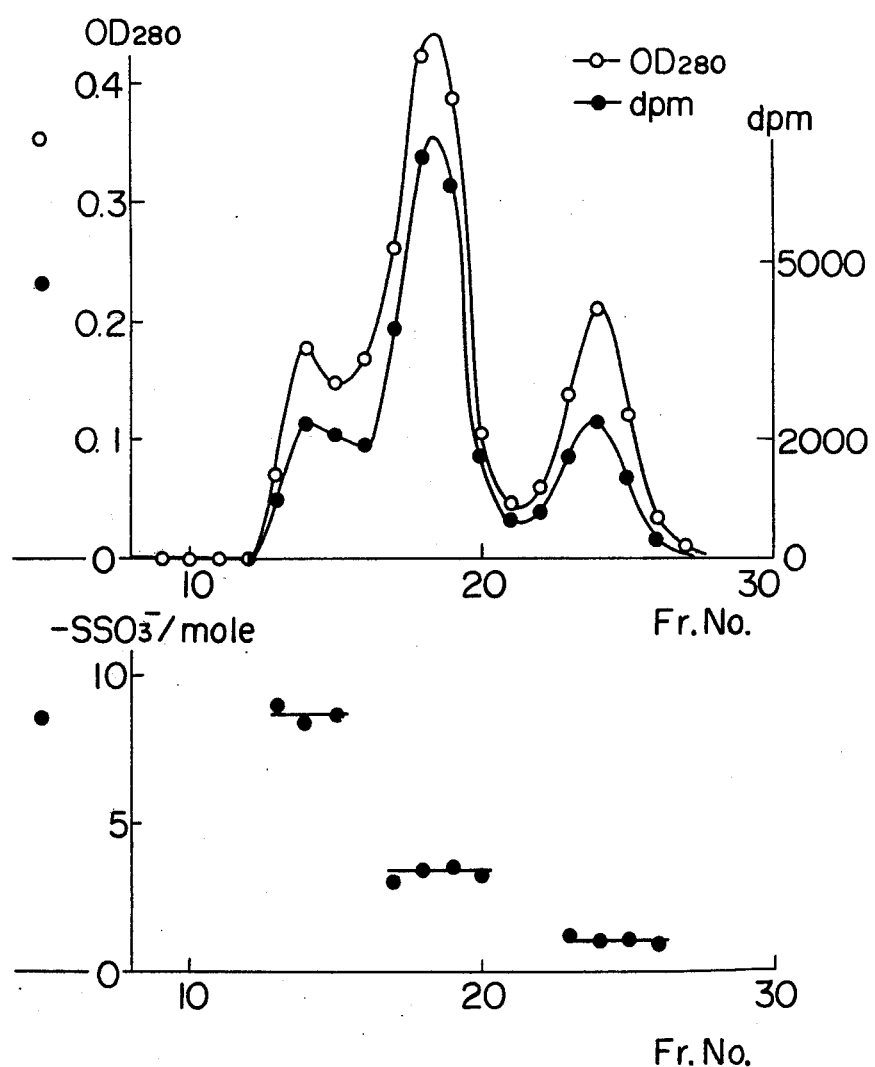

The radioactivities of the samples were measured by $OD_{280}$ of each fraction and with liquid scintillation counter, with the results shown in FIG. 8.

EXAMPLE 4

(Fractionation of heavy chains and light chains)

To an aqueous solution containing 100 mg of human γ-globulin II, 0.4 g of $Na_2SO_3$ and 0.2 g of $Na_2S_4O_6$.$2H_2O$ were added, and pH of the system was adjusted to 9.0 with 1N HCl, followed by reaction for 48 hours at room temperature. After the reaction the minor amount of insoluble matter formed in the system was centrifugally eliminated. The reaction liquid then was dialyzed using Visking tube against 2.5 liters of water at 5° C. for 15 hours, and further with 2.5 liters of an aqueous solution of 1N-propionic acid, at 5° C. for 28 hours. Subjecting the dialyzate to the chromatography using Sephadex G75 column (3.5 $\phi$ cm × 111 cm) equilibrated with 1N-propionic acid, the polypeptide chains were fractionated. As demonstrated in FIG. 9, three peaks were observable in the graph, which were confirmed to be, by the order of greater molecular weight, of unfractionated S-sulfonated immunoglobulin, S-sulfonated H chains, and S-sulfonated L chains. The identification was performed by immunological means such as Ouchterlony method and immuno-electrophoresis, as well as by chemical analysis such as amino acid analysis, hexose content measurement, etc.

Figure 9:
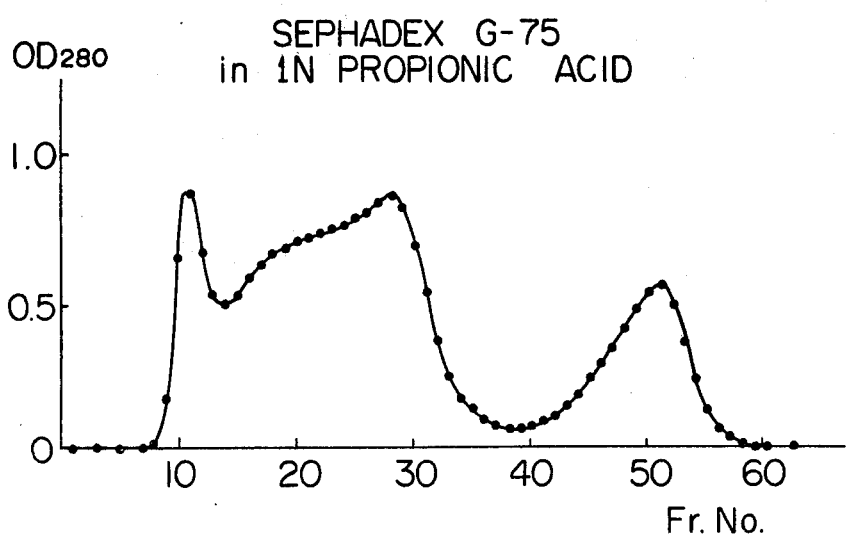

From the results shown in FIGS. 8 and 9, the following conclusions are derived.

1. Since the first peak was identified to be of unfractionated S-sulfonated immunoglobulin, the second peak, to be of S-sulfonated H chains, and the third peak, S-sulfonated L chains, by the immunological and chemical methods, referring to FIG. 9, from left to right, it is only logical to conclude that similarly the three peaks in FIG. 8 are, from left to right, contributable to unfractionated S-sulfonated immunoglobulin, S-sulfonated H chains, and S-sulfonated L chains, respectively. The difference between the chromato-patterns are caused by the presence of urea in the reaction system of the former.

2. Referring to FIG. 8, from the amount of protein in the L chains forming the third peak, the molar concentration was calculated, and from the molar concentration and radioactivity level, it was discovered that the L chains forming the third peak contains 1.0 S–$SO_3$* group. In the same manner, the number of S–$SO_3$* groups in the H chains of second peak was calculated to be 3.4, that in the unfractionated S-sulfonated immunoglobulin, 8.8, and that in the mixture before the charging into the chromato-column, 8.6. As already explained, there is one disulfide bond linking L chain and H chain, while average 2.5 disulfide bonds between two H chains. Consequently, human immunoglobulin contains average 4.5 interchain disulfide bonds.

3. According to the chromato-pattern of FIG. 8, the greatest part of the S-sulfonated immunoglobulin containing average 8.6 S–$SO_3$* groups is separable into H chains and L chains. Therefore, it can be understood that the interchain disulfide bonds are selectively cleaved, while the intrachain disulfide bonds are left substantially intact.

EXAMPLE 5

(One embodiment of reaction condition)

133 Milliliters of human γ-Globulin I was dissolved in 1667 ml of 0.06M phosphate-buffer (pH 8.2) containing 2.5% glycine. To the solution 7.0 g of $Na_2SO_3$ dissolved in 100ml of same buffer and 4.4 g of $Na_2S_4O_6.2H_2O$ dissolved in 100 ml of the same buffer were added, and reacted at 45° C. for 3 hours. The reaction liquid was dialyzed for 6 hours against 20 liters of buffer saline composed of sodium salt, using Dow Chemical's beaker, Ultrafilter b/HFU-1. The outer liquid of dialysis was exchanged at every 2 hours. The dialyzate was concentrated to a volume of 180 ml by the same filter, and to which 50 g of glycine was added.

The solution was sterile filtered through a 0.25 μ membrane, poured into 10 ml vials by 5.0 ml each, and lyophilized. The anticomplement activity $CH_{50}$ of the sterile solution at 50% concentration was 4.3%.

EXAMPLE 6

(Comparison of antibody activities to antigens in the experiments using $Na_2S_4O_6$ or $Cu^{++}$ as the oxidizing agent)

Condition I

To 67 ml of human γ-Globulin I, 7.1 g of $Na_2SO_3$, and 0.43 g of $Na_2S_4O_6.2H_2O$, 0.1M tris HCl buffer solution containing 2.5% glycine was added to make the total volume 1.0. After 3 hours reaction at 45° C., the reaction liquid was dialyzed using Dow Chemical's beaker, Ultrafiller b/HFU-1, and the dialyzate was concentrated to a volume of 200 ml, sterile filtered through seitz' 0.25μfilter, lyophilized with addition of 2.5 g of glycine, and diluted with water to 5.0% solution. The antibody activities of the sample solution were as shown in Table 2.

Condition II

The reaction and treatments under Condition I above were repeated except that the reaction temperature and time were changed to 25° C. and 24 hours.

Condition III

The reaction and treatments under Condition I were repeated except that $Na_2S_4O_6.2H_2O$ was replaced by 0.16 g of $CuSO_4.5H_2O$.

The solution of immunoglobulin derivatives obtained under the foregoing Conditions I through III were determined of their antibody activities to various antigens, with the results as shown in Table 2.

Table 2

| Antigen Reaction Condition | Diphtheria (units/ml) | Measles (units/ml) | Rubella (relative) | Mumps (relative) |
|---|---|---|---|---|
| Intact | 0.8 | 6.7 | 171 | 11 |
| I ($Na_2S_4O_6$, 45° C-3hrs) | 0.8 | 5.0 | 170 | — |
| II ($Na_2S_4O_6$, 25° C-24hrs) | — | 4.4 | — | 10 |
| III ($Cu^{++}$ 45° C-3hrs) | <0.1 | <2 | — | — |

From the data given in Table 2 above, the following conclusions may be reached.

1. When tetrathionate was used (Condition I), the titre of diphtheria of the S-sulfonated immunoglobulin is substantially equivalent with that of native immunoglobulin, but when cupric ion was used (Condition III), the immunoglobulin derivative shows almost no activity.

2. Concerning the titre of measles, the S-sulfonated immunoglobulin which has been oxidized with tetrathionate (Conditions I and II) retained more than 60% of that of the native immunoglobulin, but that oxidized with cupric ion (Condition III) had the activity dropped to less than 30%.

From those facts it can be understood that when cupric ion is used, the reduction in antibody activity is greater than the case wherein tetrathionate is used.

EXAMPLE 7

(In vivo anticomplement test of S-sulfonated globulin)

In the manner similar to Condition I of Example 6, human S-sulfonated immunoglobulin was obtained.

Three milliliters of the 5% buffered saline solution containing 2.5% glycine, pH 7.4, 3ml of buffered saline alone as the Control, and 1 ml of 15% untreated human immunoglobulin I in buffered saline solution containing 2.5% of glycine, also as the Control, were intravenously administered to female guinea pigs of body weight 200 – 300 g, and the test bodies' serum complement levels were measured with the serums of 1.0 ml each extracted by cardio-puncture at regular intervals.

The results were as shown in Table 10. From FIG. 10 it can be understood that abrupt drop in serum complement level was observed in the test bodies after the intravenous injection of intact human immunoglobulin, which was nil with the similar administration of human S-sulfonated immunoglobulin. Also occasionally trembling was observed with the guinea pigs after the injection of the former, which was again nil with the guinea pigs to which the S-sulfonated immunoglobulin was intravenously injected. From those fact it is safetly expected that the immunoglobulin derivative of the invention is free of untoward reaction also in vivo.

EXAMPLE 8

(Durability of rabbit S-sulfonated immunoglobulin in vivo and re-formation of disulfide bonds)

a. Preparation of Rabbit anti BSA-DNP antibody:

Bovine serum albumin (BSA) was reacted with dinitrofluorophenol to form a compound which will be hereinafter referred to by the abbreviation, BSA-DNP, BSA-DNP was injected to rabbits (Species New Zealand White, male) at their foot pads, together with Freund's complete adjuvant and immunized. On 30th day after the injection, the rabbits were bled from the corotid artery. Thus obtained antiserum was treated in the manner known per se, by the precipitation process with 45% saturated ammonium sulfate, and rabbit anti BSA-DNP immunoglobulin was obtained.

b. Preparation of samples:

Condition 1

The anti BSA-DNP immunoglobulin was hydrolyzed at 37° C. for 24 hours together with 1% by weight to the immunoglobulin of pepsin, according to A. Nisonoff's method [Arch. Biochem. Biophys., 89, 230 (1960)]. The hydrolysate was subjected to chromatography with Sephadex G 150 column, and F (ab')$_2$ fragment was obtained.

Condition 2

250 Milligrams of the anti BSA-DNP immunoglobulin, 180 mg of $Na_2SO_3$, and 79 mg of $Na_2S_4O_6.2H_2O$ were dissolved in 25 ml of 0.1M tris HCl containing 2.5% glycine (pH 8.2), and reacted at 37° C. for 4 hours. The reaction liquid was dialyzed for 24 hours against buffered saline (pH 7.4), to provide that rabbit S-sulfonated immunoglobulin.

Condition 3

The above-specified BSA-DNP immunoglobulin was used as it was.

C. Measurement of turn over rate and durability

The samples formed as above were each formulated into the solutions of 5% concentration.

The sample solutions were intravenously injected to rabbits (Species New Zealand White, male, sample 1 to three rabbits, sample 2, to three rabbits, and sample 3, to two rabbits), by the dosage of approximately 3 ml. The test animals were bled at predetermined intervals, and their plasma were extracted. The anti ESA-DNP activity in the plasma was determined by passive hemagglutination reaction [T. Matsuhashi, Chemistry & Biology, 9 396 ('71)] in which BSA-DNP was fixed on sheep red blood cells using glutaraldehyde and microtitre method was employed, with the results as shown in FIG. 11.

As clearly demonstrated in FIG. 11, the in vivo turn over rate is extremely short for the commercial F $(ab')_2$, which suggests short duration of pharmaceutical efficacy. In contrast thereto, the S-sulfonated immunoglobulin shows approximately the same half life with that of native immunoglobulin, promising the durable pharmaceutical efficacy.

d. Measurement of hemolytic activity of antibody

The specified native anti BSA-DNP immunoglobulin was intravenously injected to the rabbits, and their plasma was collected 10 minutes after the injection, which was diluted by 100 vol. times and reacted with guinea pig complement and sheep red blood cells on which BSA-DNP was adsorbed by tannic acid, at 37° C. for an hour.

The intact antibody of Condition 3 caused 100% hemolysis, while the $F(ab')_2$ of Condition I and S-sulfonated sample of Condition 2 showed no hemolytic activity.

As to the plasma taken from the rabbits 24 hours after the injection, the product of Condition 2 caused 100% hemolysis in the test similar to the above.

This phenomenon is probably due to the re-conversion of S-sulfonated immunoglobulin to native immunoglobulin in vivo, i.e., the reduction of -$S-SO_3$ to -SH and re-formation of disulfide bond.

e. Measurement of reduction in vivo label concentration:

Thirty (30) mg of rabbit immunoglobulin, 21 mg of $^{35}S$-$Na_2SO_3$, and 13 mg of $Na_2S_4O_6.2H_2O$ were dissolved in 3 ml of 0.1M tris HCl containing 2.5% glycine, (pH, 8.2), and reacted at 45° C. for 3 hours. The reaction liquid was dialyzed for 24 hours against buffered saline (pH 7.4), and thus $^{35}S$-labelled rabbit S-sulfonated immunoglobulin was prepared.

The above sample diluted to 5% concentration was intravenously injected to two rabbits (New Zealand White, male) by 1.5 to each, and the rabbits' plasma were extracted at predetermined intervals, by 0.5 ml per rabbit. The radioactivities of the plasma was measured by liquid scintillation counter, with the result as shown in Table 3 below.

Table 3

| Bleeding Time After Intravenous Injection | Residual Radioactivity in Blood | |
| --- | --- | --- |
| | Rabbit A | Rabbit B |
| 15 mins | 100 % | 100 % |
| 3 hrs | 64 | 64 |
| 7 | 34 | 36 |
| 24 | 9.5 | 8.0 |
| 48 | 2.2 | 1.0 |
| 72 | 0.7 | 0 |

From the results shown above, it can be understood that -$S-SO_3$* groups in the S-sulfonted immunoglobulin are cleaved in the blood.

As demonstrated by the foregoing Examples, according to the invention it is possible to selectively cleave the disulfide bonds linking H chains and L chains in native immunoglobulin, and the so produced sulfur atoms can be S-sulfonated. The number of cleavage can be furthermore controlled to, on the average, the range of 3 - 5, around 4.5 that is the average number of interchain disulfide bonds of native immunoglobulin, and the sulfur atoms formed upon cleavage can be S-sulfonated.

Such novel immunoglobulin derivatives of the invention possess the anticomplement activity far lower than that of native immunoglobulin as illustrated in the Examples, and consequently cause far less untoward reactions of anaphylactic factors. Thus the derivatives are injectable not only intramuscularly but also intravenously. Moreover, the novel immunoglobulin derivatives of the invention exhibit almost equivalent antigen-binding activity to that of native immunoglobulin, and therefore possess excellent binding activities to various antigens.

It is known in the past to remove aggregates from the immunoglobulin prepared by fractionation, by adsorption or sedimentation with active carbon or polymer substances. But still the so treated immunoglobulin not rarely caused untoward reactions of the injection recipient. Furthermore, reaggregation is observed in the so treated immunoglobulin during storage. Thus the product is still incomplete as the safety injectable composition [L.A. Hanson & B. G. Johanson; Int. Arch. Allergy. 31, 380 (1967)]

It is already mentioned and demonstrated that the immunoglobulin derivatives of the invention exhibit far less untoward reactions and excel in this respect (of FIG. 2).

Also the immunoglobulin derivatives of this invention maintain the antigen-binding activity over a prolonged period as shown in Example 8. Furthermore, the S-sulfonate groups in the derivatives are re-converted to disulfide bonds in vivo, while the sulfonate groups are discharged out of the body. Thus ultimately the derivatives are re-converted to the native immunoglobulin. For this reason also the S-sulfonated immunoglobulin of the invention has apparent advantages over the known S-alkylated immunoglobulins.

As has been explained, it is again apparent that the novel immunoglobulin derivatives of the invention are suitable as the pharmaceutically effective ingredient of not only for intramuscular injection but also for intravenous injection.

The novel immunoglobulin derivatives of the invention can provide water-soluble compositions for injectable liquid, when blended with solubilizing agents such as glycine, sodium phosphate, citrate, sodium chloride, and the like, at suitable concentrations. Furthermore, the composition may be dissolved in water at the concentrations, say, 1 - 20% by weight, preferably 2 - 10% by weight, to provide intravenously injectable compositions.

Obviously, the S-sulfonated immunoglobulin of the invention is useful not only for human therapy, but also for treating animals such as cow, horse, pig, sheep, dog, etc. As the immunoglobulin derivatives for treating animals, preferably the native immunoglobulines obtained from the respective animals are S-sulfonated according to the present invention.

We claim:

1. Novel immunoglobulin derivatives which are substantially free from oxidizing metal ions such as cupric ion comprising immunoglobulin in which the interchain disulfide bonds are predominantly cleaved, on the average 3 to 5 of the interchain disulfide bonds or the inter- and intra-chain disulfide bonds being cleaved, and so produced sulfur atoms (S—) are S-sulfonated (-S-SO$_3$).

2. The novel immunoglobulin derivatives of claim 1, in which on the average approximately 3 - 4.5 interchain disulfide bonds of immunoglobulin are substantially selectively cleaved, and the so produced sulfur atoms are S-sulfonated.

3. The novel immunoglobulin derivative according to claim 1, in which on the average approximately 4.5 interchain disulfide bonds of immunoglobulin are substantially selectively cleaved, and so produced sulfur atoms are S-sulfonated.

4. Immunoglobulin which is characterized in that
   1. on the average 3 to 5 interchain disulfide bonds, or inter- and intra-chain disulfide bonds, of immunoglobulin are cleaved and so formed sulfur atoms (S-) are S-sulfonated (-S-SO$_3$),
   2. it has the titre of anti-diphtheria of 1.0 international unit (I.U.)/ml. at its concentration of 10.0% by weight, and
   3. it is substantially free from oxidizing metal ions.

5. A water-soluble composition which comprises an immunoglobulin derivative which is substantially free from oxidizing metal ions in which on the average 3 to 5 interchain disulfide bonds, or inter- or intra-chain disulfide bonds, of native immunoglobulin are cleaved, and so formed sulfur atoms are S-sulfonated (S-SO$_3$), and which exhibits the anti-diphtheria titre of at least 1.0 I.U./ml at the concentration of 10.0% by weight, and a harmless solubilizing agent of said immunoglobulin derivative.

6. Aqueous injectable compositions which comprise an immunoglobulin derivative of claim 4, the harmless solubilizing agent of the immunoglobulin derivatives, and water.

7. A process for the preparation of immunoglobulin derivatives which comprises reacting native immunoglobulin with
   A. a compound capable of forming tetrathionate ion, and
   B. a compound capable of forming sulfite ion in water, in the substantial absence of oxidizing metal ion to thereby cleave on the average 3 to 5 interchain disulfide bonds, or inter- and intra-chain disulfide bonds, of the native immunoglobulin, and S-sulfonating (S-SO$_3$) the so formed sulfur atoms.

8. The process for making immunoglobulin derivatives according to claim 7, in which the reaction is effected at the pH ranging from 3.5 to 10.

9. The process for making immunoglobulin derivatives according to claim 8, in which the reaction is effected at the temperature within the range of 10° - 50° C.

10. The process of claim 7 in which compound (A) is tetrathionic acid, sodium tetrathionate, potassium tetrathionate, or ammonium tetrathionate, and compound (B) is sulfurous acid, sodium sulfite, potassium sulfite or sodium bisulfite.

11. The process of claim 7 in which, on the average, 4.5 interchain disulfide bonds of immunoglobulin are selectively cleaved, and the so produced sulfur atoms are S-sulfonated.

12. The process of claim 11 wherein the reaction temperature is within the range of 15°- 48° C. and the pH during the reaction is maintained within the range of 6 to 9.

13. The process of claim 7 wherein the compound (A) and the compound (B) are each present in an amount of from 2 to 100 molar times the interchain, or inter- and intra-chain disulfide bonds of the starting native immunoglobulin to be cleaved.

* * * * *